United States Patent [19]

Daigle

[11] Patent Number: 4,712,254
[45] Date of Patent: Dec. 15, 1987

[54] HEADBAND AND EYEPIECE COMBINATION

[76] Inventor: Ronald H. Daigle, 20 Nickerson St., Cranston, R.I. 02910

[21] Appl. No.: 902,180

[22] Filed: Aug. 29, 1986

[51] Int. Cl.$^4$ ............................................. A61F 9/02
[52] U.S. Cl. ............................................ 2/452; 2/454; 2/171; 2/DIG. 11
[58] Field of Search ............ 2/426, 454, 452, 171, 2/173, 10, DIG. 11; 351/155, 158

[56] References Cited

U.S. PATENT DOCUMENTS

| | | | |
|---|---|---|---|
| 542,636 | 7/1895 | Goldstein | 2/10 |
| 700,587 | 5/1902 | Waldron | 2/10 |
| 2,179,719 | 11/1939 | Goskey | 2/10 |
| 4,277,847 | 7/1981 | Florio | 2/171 X |
| 4,393,519 | 7/1983 | Nicastro | 2/DIG. 11 X |
| 4,520,510 | 6/1985 | Daigle | 2/454 X |
| 4,521,922 | 6/1985 | Mitchell et al. | 2/171 |
| 4,616,367 | 10/1986 | Jean, Jr. | 2/452 |

*Primary Examiner*—Peter Nerbun
*Attorney, Agent, or Firm*—Salter & Michaelson

[57] ABSTRACT

A headband and eyeglasses combination comprises a headband element which is receivable on the head of a wearer and has an open pocket formed therein, an eyepiece which is receivable in the pocket and a mounting assembly for mounting the eyepiece on the headband element. The eyepiece is mounted on the headband element so that it is alternatively positionable in a retracted first position wherein it is received in the pocket for use of the device as a conventional headband or an operative second position wherein it extends from the headband element for use of the device as a headband and eyeglass combination.

8 Claims, 6 Drawing Figures

HEADBAND AND EYEPIECE COMBINATION

BACKGROUND AND SUMMARY OF THE INVENTION

The instant invention relates to headbands and to the use thereof in combination with eyeglasses, including sunglasses, and more particularly the instant invention relates to a combination device which may be alternatively worn as a headband or as a headband and eyeglasses combination.

It is well recognized that both headbands and sunglasses have become highly popular in recent years. In this connection, headbands have become popular as fashionable articles of ornamentation, and they have also become popular for practical reasons, such as for their effectiveness in retaining the hair or absorbing the perspiration of those engaged in rigorous physical activity. Sunglasses have also become popular as highly fashionable articles of ornamentation, and they have also become popular for their obvious practical benefits. However, sunglasses have generally had the disadvantage that it has been necessary for some type of retaining straps or the like to be used in combination with sunglasses in order to retain them on the heads of wearers during rigorous physical activity.

The convertible headband construction disclosed in the applicant's U.S. Pat. No. 4,520,510 which issued on June 4, 1985, was developed in recognition of the increased popularity of both sunglasses and headbands, and it represents the closest prior art to the subject invention of which the applicant is aware. The convertible headband disclosed in this patent comprises an elongated flexible band which is snugly receivable in encircling relation on the head of a wearer and which has a pair of eye openings therethrough, a flexible flap which is attached to the band adjacent the eye openings, and an eyepiece which covers the eye openings. The flap is alternatively positionable in a first position wherein it is wrapped around the band for covering the eye openings therein and a second position wherein it is folded adjacent the band so that the eye openings are unobstructed. Accordingly, this device can alternatively be worn as a conventional headband by positioning the flexible flap so that it covers the eye openings and then positioning the band on the head of a wearer so that it extends across the forehead, or as a pair of sunglasses by positioning the flap so that it is folded alongside the band and positioning the band on the head of a wearer so that the eye openings in the band are aligned with the eyes of the wearer. However, while this device has proven to be an effective headband and sunglasses combination, it has been found that some persons object to the use of a handband which extends across the eye area in order to position lenses in front of the eyes. It has also been found that some persons prefer to use headbands of more conventional construction which do not include flaps for covering eye openings therein. Accordingly, the applicant has now developed a new headband and eyeglasses combination which is preferably embodied as a headband and sunglasses combination and which represents an effective alternative to the convertible headband construction disclosed in the applicant's aforesaid U.S. patent.

Other devices representing prior art to the subject invention of which the applicant is aware are disclosed in the U.S. Pat. Nos. 2,385,405 to Crowther; 3,173,147 to Gross et al; 4,176,410 to Matthias; 4,304,005 to Danley, Sr. and 4,393,519 to Nicastro. However, since the devices disclosed in these references are believed to be less pertinent to the subject invention than the disclosures of the applicant's own aforesaid U.S. patent, they are believed to be of only general interest.

The headband and eyeglasses combination of the instant invention generally comprises a headband element having an open pocket formed therein which opens outwardly along an edge of the headband element, an eyepiece which is receivable in the pocket, and means for securing the eyepiece to the headband element so that the eyepiece is alternatively positionable in a retracted first position wherein it is received in the pocket and an operative second position wherein it is disposed adjacent a side edge of the headband element. The headband element is constructed so that it is receivable in encircling relation on the head of a wearer in a position wherein the pocket portion thereof extends across the forehead of the wearer and opens downwardly along the lower edge of the headband element, and the means securing the eyepiece to the headband element is constructed so that when the headband element is received on the head of a wearer and the eyepiece is in the second position thereof, it extends in front of the eyes of the wearer and so that when the eyepiece is in the retracted first position thereof, it is substantailly concealed in the pocket. The eyepiece is preferably embodied as a sunglasses-type eyepiece, and hence it preferably comprises a pair of tinted lenses. The lenses of the eyepiece are preferably hingeable connected, and the means securing the eyepiece to the headband element is preferably adapted for secruing the eyepiece so that it is slidable between the first and second positions thereof. The means for securing the eyepiece to the headband element preferably comprises first and second track elements which are mounted on a frame in the pocket in spaced, substantially transverse relation to the extent of the headband element, and first and second pin elements on the eyepiece which are slidably received in the first and second track elements, respectively, for slidably mounting the eyepiece on the headband element.

For use of the combination device of the instant invention as a conventional headband, the eyepiece is positioned in the retracted first position and the headband element is positioned in encircling relation on the head of a wearer so that it extends across the forehead and so that the pocket opens downwardly above the eyes of the wearer. The device may thereafter be alternatively worn as a headband with a pair of eyeglasses attached thereto by sliding the eyepiece downwardly so that it is removed from the pocket and positioned in front of the eyes of the wearer. In the preferred embodiment of the combination device of the instant invention, this operation can be quickly and easily effected by sliding the eyepiece downwardly in the track elements to position it in front of the eyes of the wearer. Further, in the preferred embodiment of the combination device of the instant invention, the eyepiece comprises a pair of hingeably connected tinted lens elements, and this enables the eyepiece to be more effectively adapted to the contours of a wearer's face, and it also enables the combination headband and eyeglasses device to be easily and neatly folded so that it can be effectively transported in a pocket of the wearer.

Accordingly, it is a primary object of the instant invention to provide an effective headband and eyeglasses combination.

Another object of the instant invention is to provide a headband and eyeglasses combination comprising a headband element having a pocket therein and an eyepiece which is mounted on the headband element so that it is slidable between a retracted first position wherein it is received in the pocket and a second position wherein it is disposed alongside of the headband element.

A still further object of the instant invention is to provide a headband and eyeglasses combination comprising a headband element which is receivable in encircling relation on the head of a wearer so that it extends across the forehead of the wearer and an eyepiece which is mounted on the headband element and downwardly slidable to a position wherein it is disposed in front of the eyes of the wearer.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention.

DESCRIPTION OF THE INVENTION

Figure 1:
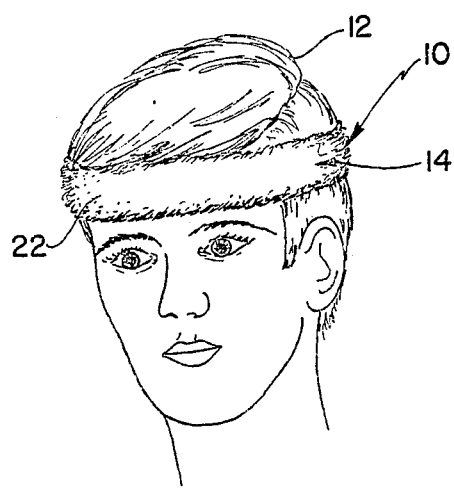
FIG. 1 is a perspective view of the headband and eyeglasses combination of the instant invention mounted on the head of a wearer with the eyepiece in the retracted first position thereof.

Referring now to the drawings, the headband and eyeglasses combination of the instant invention is illustrated in FIGS. 1 through 6 and generally indicated at 10. The headband and eyeglasses combination 10 is adapted to be worn on the head 12 of a wearer in the manner illustrated in FIGS. 1 and 2, and it comprises a headband element generally indicated at 14, an eyepiece generally indicated at 16, and a mounting assembly generally indicated at 18 which is adapted for mounting the eyepiece 16 on the headband element 14 so that it is alternatively positionable in the retracted first position illustrated in FIGS. 1 and 4 or the downwardly extended operative second position illustrated in FIGS. 2, 3 and 5.

Figure 2:
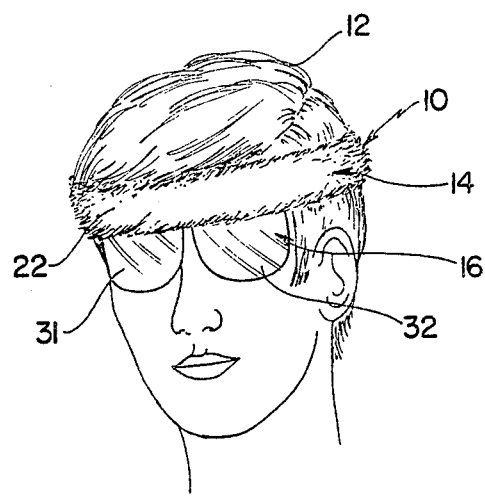
FIG. 2 is a similar view with the eyepiece in the downwardly extended operative second position thereof.
Figure 3:
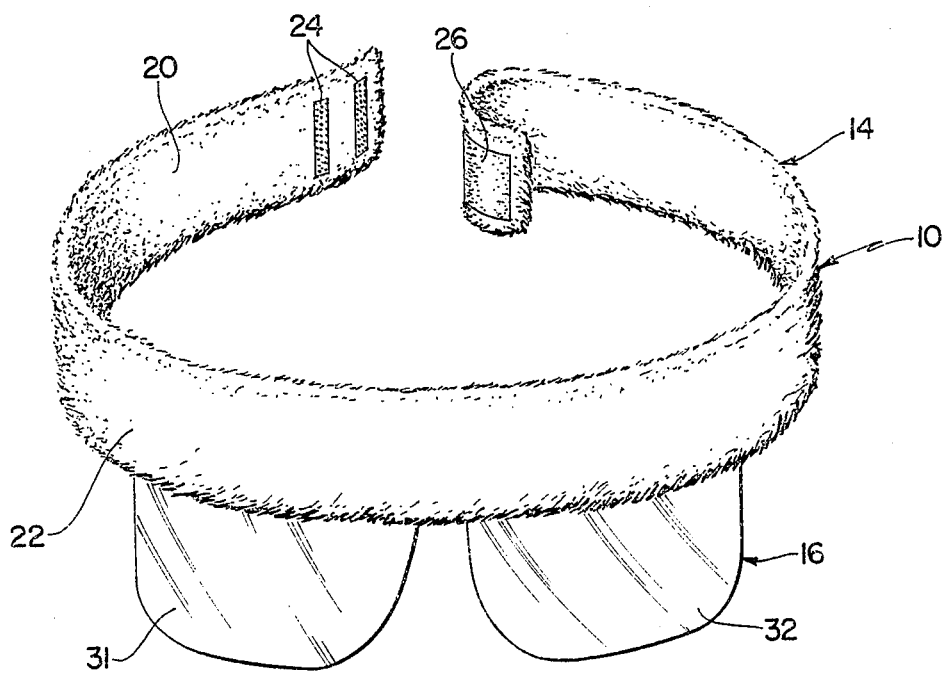
FIG. 3 is a perspective view of the headband and eyeglasses combination per se with the eyepiece in the downwardly extended second position.
Figure 4:
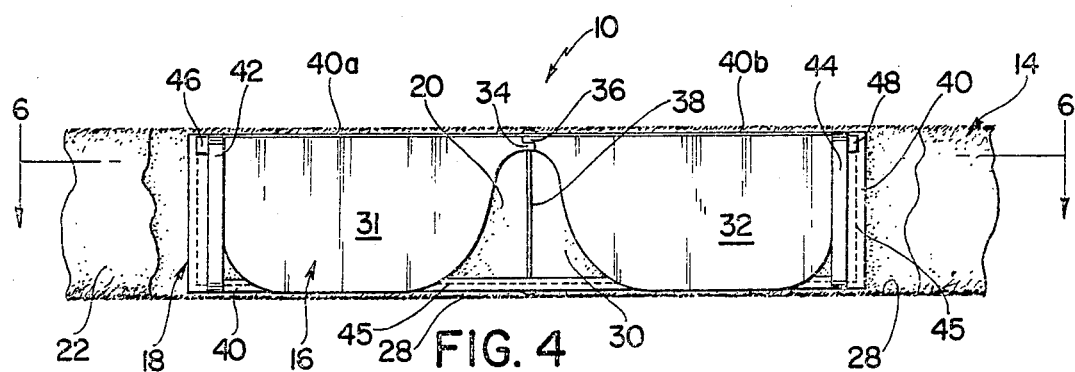
FIG. 4 is a fragmentary plan view of the headband and eyeglasses combination with the eyepiece in the retracted first position.
Figure 5:
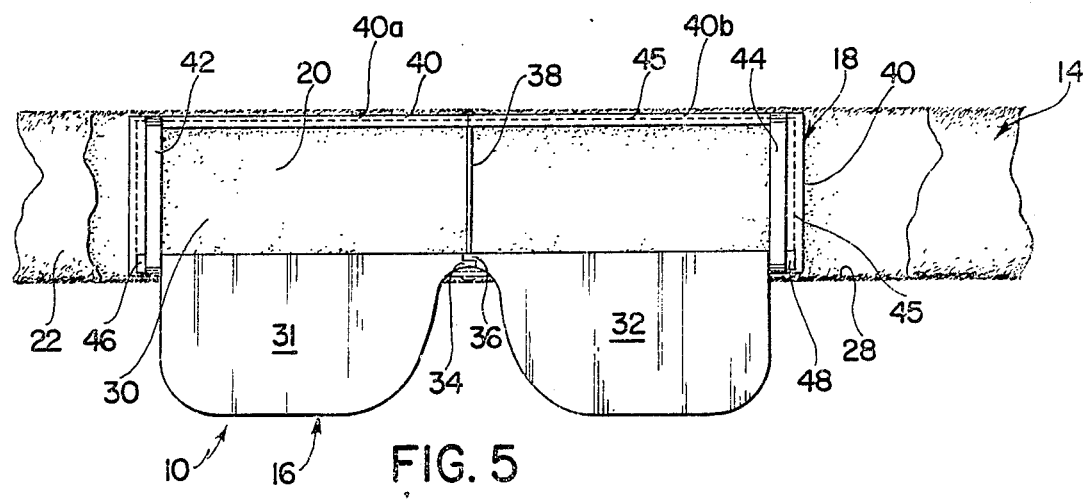
FIG. 5 is a similar view with the eyepiece in the downwardly extended second position.
Figure 6:
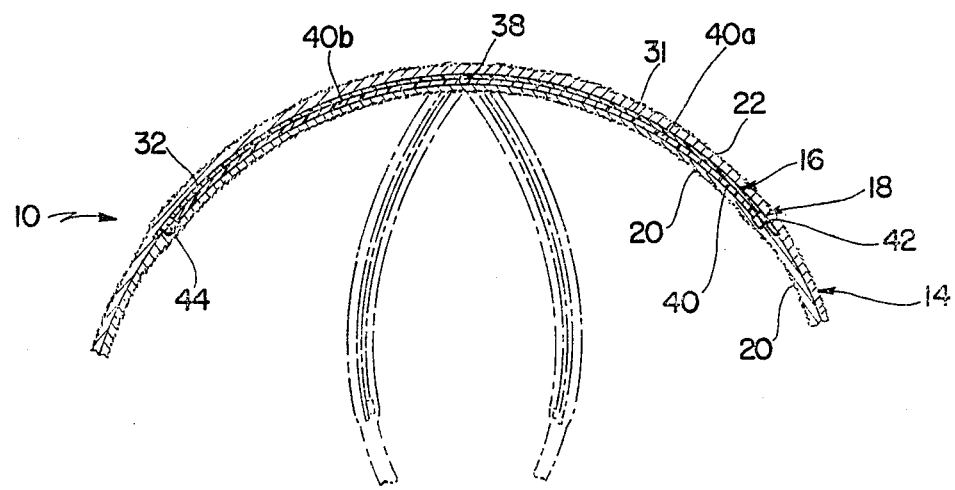
FIG. 6 is a sectional view taken along line 6—6 in FIG. 4.

The headband element 14 as herein embodied is made in an elongated strap-like configuration from a flexible, resilient fabric material, such as a resilient terrycloth, and it is preferably made in a multi-layered construction so that it has separate inner and outer layers 20 and 22, respectively, which define the inner and outer sides of the headband element 14. Provided on the inner layer 20 adjacent one terminal end of the headband element 14 are fastening elements 24, and a fastening element 26 is provided on the outer layer 22 adjacent the opposite terminal end of the headband element 14. The fastening elements 24 and 26 preferably comprise hook and loop type fastening elements, such as Velcro (Velcro USA Inc. TM) fastening elements, which are receivable in interengagement for securing the headband element 14 in a closed loop configuration on the head 12 of a wearer. It will be understood, however, that the use of a variety of other fastening elements is contemplated and that continuous closed loop configurations for the headband element are also contemplated. In any event, the headband element 14 is dimensioned to be snugly received on the head 12 so that it extends across the forehead portion thereof as illustrated in FIGS. 1 and 2. Formed at an intermediate point in the extent of one edge of the headband element 14 is an elongated opening 28 which provides access to an interior area or pocket 30 which is formed between the inner and outer fabric layers 20 and 22, respectively.

The eyepiece 16 is preferably made from a suitable resiliently flexible transparent plastic material, and it comprises a pair of lens elements 31 and 32 which are preferably made in suitably tinted or colored constructions to enable them to be effectively utilized as sunshields or sunglasses. The lens elements 31 and 32 include hinge portions 34 and 36, respectively, which are hingeably interconnected by means of a hinge pin 38 to enable the eyepiece 16 to conform more closely to the contour of the face of a wearer and also to enable the eyepiece 16 to be folded so that the headband and eyeglasses combination 10 can be conveniently transported and stored when not in use. The eyepiece 16 is dimensioned to be received in the pocket 30 in the headband element 14, and it is dimensioned so that the lens elements 31 and 32 are receivable over the eyes of a wearer for providing sun protection therefor. The eyepiece 16 and the headband element 14 are preferably dimensioned so that when the eyepiece is received in the pocket 30 it is substantially concealed from view by the headband element 14.

The mounting assembly 18 is preferably made of a durable and substantially rigid plastic material, and it preferably comprises an elongated, substantially rectangular frame 40 which is received and secured in the pocket 30 and includes hingeably connected first and second frame halves 40a and 40b, and first and second track elements 42 and 44, respectively, which are secured on the frame 40. The frame 40 is preferably of slightly greater length than the width of the eyepiece 16, and it is preferably secured in the pocket 30 with stitching 45 or the like. The track elements 42 and 44 are preferably integrally formed with the frame 40, and they are positioned thereon so that they extend in substantially transverse relation to the headband element 14. The track elements 42 and 44 are positioned on the frame 40 in spaced relation adjacent the opposite ends thereof so that they cooperate to define spaced slots adjacent the opposite ends of the frame 40 which extend in substantially transverse relation to the headband element 14 adjacent opposite ends of the elongated opening 28. Also included in the mounting assembly 18 are first and second pins 46 and 48 which are attached to the eyepiece 16 adjacent the upper side extremities thereof. The pins 46 and 48 are received in the slots defined by the track elements 42 and 44 and the frame 40 to mount the eyepiece 16 so that it is slidable between the first or retracted position illustrated in FIG. 4 and the second or downwardly extended operative position illustrated in FIG. 5. The pin 38 is mounted in the central portion of the frame 40 so that it extends between the upper and lower extremities thereof for guiding the eyepiece 16 so that it is easily slidable between the first and second positions thereof. Further, the pins 46 and 48 and the track elements 42 and 44, and the pin 38 and the hinge portions 34 and 36 are preferably dimensioned so that when the eyepiece 16 is in its downwardly extended second position, it remains substantially parallel to the headband element 14, and it is not normally outwardly or inwardly hingeable with respect thereto.

For use and operation of the headband and eyeglasses combination 10, the headband element 14 is positioned in encircling relation on the head 12 so that it extends across the forehead portion thereof with the opening 28 of the pocket 30 disposed above the eyes. Once the headband element 14 has been installed on the head 12 in this manner, the headband and eyeglasses combination 10 can be alternatively worn as a conventional headband in the manner illustrated in FIG. 1 or as a combination headband and eyeglasses in the manner illustrated in FIG. 2. In this regard, as illustrated in FIG. 1, when the eyepiece 16 is in the retracted first position thereof, it is substantially concealed by the headband element 14 so that the headband and eyeglasses combination can be worn as a conventional headband. However, by sliding the eyepiece 16 downwardly in the mounting assembly 18 so that it passes outwardly through the opening 28 and is positioned adjacent the lower edge of the headband element 14, the headband and eyeglasses combination can be worn as a combination headband and eyeglasses in the manner illustrated in FIG. 2. Further, once the eyepiece 16 is returned to its retracted first position and the headband and eyeglasses combination 10 is removed from the head 12, the combination device 10 can be neatly folded by hinging the frame 40 and the eyeiece 16 along the hinge pin 38 and folding the headband element 14 around the eyepiece 16 and the mounting assembly 18.

It is seen, therefore, that the instant invention provides an effective headband and eyeglasses combination which is adapted to be alternatively worn as a headband or as a headband and eyeglasses combination. The headband and eyeglasses combination 10, which is preferably embodied as a headband and sunglasses combination, has a unique structure which provides a novel and pleasing appearance, and it can be effectively worn by persons engaged in rigorous physical activity. Accordingly, it is seen that the subject invention represents a significant advancement in the art which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A headband and eyeglasses combination consisting essentially of a headband element having an open pocket therein which opens outwardly along an edge thereof, said headband element being receivable in encircling relation on the head of a wearer so that it extends across the forehead of said wearer in snug engagement therewith and so that said pocket opens downwardly adjacent said forehead, a flexible eyepiece receivable in said pocket, and means securing said eyepiece to said headband element so that it is alternatively positionable in a retracted first position wherein it is received in the pocket and a second position wherein it extends downwardly from the headband element and is disposed in front of the eyes of said wearer.

2. In the headband and eyeglasses combination of claim 1, said eyepiece further characterized as comprising a pair of colored lenses.

3. In the headband and eyeglasses combination of claim 1, said securing means further characterized as mounting said eyepiece so that it is slidable between said first and second positions thereof.

4. In the headband and eyeglasses combination of claim 1, said eyepiece comprising a pair of hingeably connected lenses.

5. In the headband and eyeglasses combination of claim 3, said securing means comprising first and second spaced track elements transversely mounted on said headband element in said pocket, and first and second pin elements on said eyepiece slidably received in said first and second track elements, respectively, for slidably mounting said eyepiece on said headband element.

6. In the headband and eyeglasses combination of claim 5, said securing means further comprising a frame mounted in said pocket and extending between said track elements, said track elements being mounted on said frame.

7. In the headband and eyeglasses combination of claim 1, said eyepiece being substantially completely concealed in said pocket when it is in said retracted first position thereof.

8. In the headband and eyeglasses combination of claim 6, said eyepiece comprising a pair of hingeably connected lens elements, said frame comprising a pair of frame halves which are hingeable about substantially the same axis as said lens elements.

* * * * *